(12) United States Patent
Krishnan et al.

(10) Patent No.: US 8,280,750 B2
(45) Date of Patent: Oct. 2, 2012

(54) PATIENT DATA MINING FOR CARDIOLOGY SCREENING

(75) Inventors: Sriram Krishnan, Exton, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 64 days.

(21) Appl. No.: 12/780,012

(22) Filed: May 14, 2010

(65) Prior Publication Data

US 2010/0222646 A1 Sep. 2, 2010

Related U.S. Application Data

(62) Division of application No. 10/287,085, filed on Nov. 4, 2002, now Pat. No. 7,744,540.

(60) Provisional application No. 60/335,542, filed on Nov. 2, 2001.

(51) Int. Cl.
*A61B 5/02* (2006.01)
*A61B 5/00* (2006.01)
*G06Q 10/00* (2006.01)
*G06Q 50/00* (2006.01)

(52) U.S. Cl. ............ 705/2; 600/300; 600/301; 600/481; 705/3

(58) Field of Classification Search .................. 600/481, 600/300, 301; 705/2, 3; 707/999.1, E17.117
See application file for complete search history.

(56) References Cited

U.S. PATENT DOCUMENTS

| | | |
|---|---|---|
| 4,946,679 A | 8/1990 | Thys-Jacobs |
| 5,172,418 A | 12/1992 | Ito et al. |
| 5,307,262 A | 4/1994 | Ertel |
| 5,359,509 A | 10/1994 | Little et al. |
| 5,365,425 A | 11/1994 | Torma et al. |
| 5,508,912 A | 4/1996 | Schneiderman |
| 5,544,044 A | 8/1996 | Leatherman |
| 5,557,514 A | 9/1996 | Seare et al. |
| 5,619,991 A | 4/1997 | Sloane |

(Continued)

FOREIGN PATENT DOCUMENTS

DE 19820276 11/1999

(Continued)

OTHER PUBLICATIONS

Rao, et al. "Data Mining for Disease Management: Adding Value to Paitent Records," Electromedia vol. 68, 2000, pp. 63-67.*

(Continued)

*Primary Examiner* — Patricia Mallari
*Assistant Examiner* — Tiffany Weston
(74) *Attorney, Agent, or Firm* — Joshua B. Ryan

(57) ABSTRACT

A system and method for screening for coronary heart disease is provided. The method includes the steps of retrieving a test for assessing risk of coronary heart disease, the test including a plurality of data fields relating to coronary risk factors; accessing a database to populate the data fields with information of an individual patient; and calculating a risk assessment of the individual patient developing coronary heart disease. A system includes a first database including a plurality of structured computerized patient records; a second database including a knowledge base relating to coronary heart disease, the second database including at least one test for determining coronary heart disease risk; and a processor for retrieving the at least one test from the second database, populating the at least one test with patient information retrieved from the first database and calculating a risk assessment for at least one patient.

24 Claims, 3 Drawing Sheets

U.S. PATENT DOCUMENTS

| | | | |
|---|---|---|---|
| 5,652,842 A | 7/1997 | Siegrist, Jr. et al. | |
| 5,657,255 A | 8/1997 | Fink et al. | |
| 5,664,109 A * | 9/1997 | Johnson et al. | 705/2 |
| 5,669,877 A | 9/1997 | Blomquist | |
| 5,706,441 A | 1/1998 | Lockwood | |
| 5,724,379 A | 3/1998 | Perkins et al. | |
| 5,724,573 A | 3/1998 | Agrawal et al. | |
| 5,737,539 A | 4/1998 | Edelson et al. | |
| 5,738,102 A | 4/1998 | Lemelson | |
| 5,811,437 A | 9/1998 | Singh et al. | |
| 5,832,450 A | 11/1998 | Myers et al. | |
| 5,835,897 A | 11/1998 | Dang | |
| 5,845,253 A | 12/1998 | Rensimer et al. | |
| 5,899,998 A | 5/1999 | McGauley et al. | |
| 5,903,889 A | 5/1999 | de la Huerga et al. | |
| 5,908,383 A | 6/1999 | Brynjestad | |
| 5,924,073 A | 7/1999 | Tyuluman et al. | |
| 5,924,074 A | 7/1999 | Evans | |
| 5,935,060 A | 8/1999 | Iliff | |
| 5,937,387 A * | 8/1999 | Summerell et al. | 705/2 |
| 5,939,528 A | 8/1999 | Clardy et al. | |
| 5,991,731 A | 11/1999 | Colon et al. | |
| 6,039,688 A | 3/2000 | Douglas et al. | |
| 6,067,466 A | 5/2000 | Seiker et al. | |
| 6,076,088 A | 6/2000 | Paik et al. | |
| 6,078,894 A | 6/2000 | Clawson et al. | |
| 6,081,786 A | 6/2000 | Barry et al. | |
| 6,083,693 A | 7/2000 | Nandabalan et al. | |
| 6,125,194 A | 9/2000 | Yeh et al. | |
| 6,128,620 A | 10/2000 | Pissanos et al. | |
| 6,139,494 A | 10/2000 | Cairnes | |
| 6,151,581 A | 11/2000 | Kraftson et al. | |
| 6,173,280 B1 | 1/2001 | Ramkumar et al. | |
| 6,196,970 B1 | 3/2001 | Brown | |
| 6,212,519 B1 | 4/2001 | Segal | |
| 6,212,526 B1 | 4/2001 | Chaudhuri et al. | |
| 6,253,186 B1 | 6/2001 | Pendleton, Jr. | |
| 6,259,890 B1 | 7/2001 | Driscoll et al. | |
| 6,266,645 B1 | 7/2001 | Simpson | |
| 6,272,472 B1 | 8/2001 | Danneels et al. | |
| 6,322,502 B1 | 11/2001 | Schoenberg et al. | |
| 6,322,504 B1 | 11/2001 | Kirshner | |
| 6,338,042 B1 | 1/2002 | Paizis | |
| 6,381,576 B1 | 4/2002 | Gilbert | |
| 6,468,210 B1 | 10/2002 | Iliff | |
| 6,478,737 B2 | 11/2002 | Bardy | |
| 6,484,144 B2 | 11/2002 | Martin et al. | |
| 6,523,019 B1 | 2/2003 | Borthwick | |
| 6,529,876 B1 | 3/2003 | Dart | |
| 6,551,243 B2 | 4/2003 | Bocionek et al. | |
| 6,551,266 B1 | 4/2003 | Davis, Jr. | |
| 6,587,829 B1 | 7/2003 | Camarda et al. | |
| 6,611,825 B1 | 8/2003 | Billheimer et al. | |
| 6,611,846 B1 | 8/2003 | Stoodley | |
| 6,641,532 B2 | 11/2003 | Iliff | |
| 6,645,959 B1 | 11/2003 | Bakker-Arkema et al. | |
| 6,678,669 B2 | 1/2004 | Lapointe et al. | |
| 6,754,655 B1 | 6/2004 | Segal | |
| 6,802,810 B2 | 10/2004 | Ciamiello et al. | |
| 6,804,656 B1 | 10/2004 | Rosenfeld et al. | |
| 6,826,536 B1 | 11/2004 | Forman | |
| 6,839,678 B1 | 1/2005 | Schmidt et al. | |
| 6,903,194 B1 | 6/2005 | Sato et al. | |
| 6,915,254 B1 | 7/2005 | Heinze et al. | |
| 6,915,266 B1 | 7/2005 | Saeed et al. | |
| 6,941,271 B1 | 9/2005 | Soong | |
| 6,961,687 B1 | 11/2005 | Myers et al. | |
| 6,988,075 B1 | 1/2006 | Hacker | |
| 7,058,658 B2 | 6/2006 | Mentzer | |
| 7,130,457 B2 | 10/2006 | Kaufman et al. | |
| 7,249,006 B2 | 7/2007 | Lombardo et al. | |
| 7,307,543 B2 | 12/2007 | Rosenfeld et al. | |
| 7,353,238 B1 | 4/2008 | Gliklich | |
| 7,630,908 B1 | 12/2009 | Amrien et al. | |
| 2001/0011243 A1 | 8/2001 | Dembo et al. | |
| 2001/0023419 A1 | 9/2001 | LaPointe et al. | |
| 2001/0032195 A1 | 10/2001 | Graichen et al. | |
| 2001/0051882 A1 | 12/2001 | Murphy et al. | |
| 2002/0002474 A1 | 1/2002 | Michaelson et al. | |
| 2002/0010597 A1 | 1/2002 | Mayer et al. | |
| 2002/0019746 A1 | 2/2002 | Rienhoff et al. | |
| 2002/0026332 A1 | 2/2002 | Snowden et al. | |
| 2002/0029155 A1 | 3/2002 | Hetzel et al. | |
| 2002/0032581 A1 | 3/2002 | Reitberg | |
| 2002/0035316 A1 * | 3/2002 | Drazen | 600/300 |
| 2002/0077853 A1 | 6/2002 | Boru et al. | |
| 2002/0082480 A1 | 6/2002 | Riff et al. | |
| 2002/0087361 A1 | 7/2002 | Benigino et al. | |
| 2002/0099570 A1 | 7/2002 | Knight | |
| 2002/0107641 A1 | 8/2002 | Schaeffer et al. | |
| 2002/0123905 A1 | 9/2002 | Goodroe et al. | |
| 2002/0138492 A1 | 9/2002 | Kil | |
| 2002/0143577 A1 | 10/2002 | Shiffman et al. | |
| 2002/0165736 A1 | 11/2002 | Tolle et al. | |
| 2002/0173990 A1 | 11/2002 | Marasco | |
| 2002/0177759 A1 | 11/2002 | Schoenberg et al. | |
| 2002/0178031 A1 | 11/2002 | Sorenson et al. | |
| 2003/0028401 A1 | 2/2003 | Kaufman et al. | |
| 2003/0036683 A1 | 2/2003 | Kehr et al. | |
| 2003/0046114 A1 | 3/2003 | Davies et al. | |
| 2003/0050794 A1 | 3/2003 | Keck | |
| 2003/0065535 A1 * | 4/2003 | Karlov et al. | 705/2 |
| 2003/0108938 A1 | 6/2003 | Pickar et al. | |
| 2003/0120133 A1 | 6/2003 | Rao et al. | |
| 2003/0120134 A1 | 6/2003 | Rao et al. | |
| 2003/0120514 A1 | 6/2003 | Rao et al. | |
| 2003/0125984 A1 | 7/2003 | Rao et al. | |
| 2003/0125985 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2003/0135391 A1 | 7/2003 | Edmundson et al. | |
| 2003/0208382 A1 | 11/2003 | Westfall | |
| 2004/0067547 A1 | 4/2004 | Harbron et al. | |
| 2004/0078216 A1 | 4/2004 | Togo | |
| 2004/0184644 A1 | 9/2004 | Leichter et al. | |
| 2004/0243586 A1 | 12/2004 | Byers | |
| 2005/0187794 A1 | 8/2005 | Kimak | |
| 2005/0191716 A1 | 9/2005 | Surwit et al. | |
| 2006/0064415 A1 | 3/2006 | Guyon et al. | |
| 2006/0122864 A1 | 6/2006 | Gottesman et al. | |
| 2006/0136259 A1 | 6/2006 | Weiner et al. | |

FOREIGN PATENT DOCUMENTS

| | | |
|---|---|---|
| EP | 0596247 | 5/1994 |
| EP | 0641863 | 3/1995 |
| EP | 0917078 | 10/1997 |
| GB | 2332544 | 6/1999 |
| JP | 11328073 | 11/1999 |
| JP | 2001297157 | 10/2001 |
| WO | 9829790 | 7/1998 |
| WO | 9839720 | 9/1998 |
| WO | 0051054 | 8/2000 |
| WO | 0069331 | 11/2000 |
| WO | 0166007 | 9/2001 |
| WO | 0178005 | 10/2001 |
| WO | 0182173 | 11/2001 |

OTHER PUBLICATIONS

Kamp, et al. "Database system support for multidimensional data analysis in environmental epidemiology", The 1997 International Database Engineering & Applications Symposium; Montreal; Can; Aug. 25-27, 1997. pp. 180-188. 1997.

King, et al., "MEDUS/A: Distributing Database Management for Medical Research", Proceedinngs of Computer Networks Compcon 82, Sep. 20-23, 1982 pp. 635-642.

Boxwala et al, "Architecture for a Multipurpose Guideline Execution Engine", Proc. AMIA Symp 1999, pp. 701-705.

"Guidance for Institutional Review Boards and Clinical Investigators 1998 Update", Sep. 1998, U.S. Food and Drug Administration, http://www.fda.gov/ScienceResearch/SpecialTopics/RunningClinicalTrials/GuidancesInformationSheetsandNotices/ucm113793.htm#IRBMember.

Kassirer, "The Use and Abuse of Practice Profiles", The New England Journal of Medicine, vol. 330:634-636, Mar. 3, 1994.

Chen, et al., Do "America's Best Hospitals" Perform Better for Acute Myocardial Infarction?, The New England Journal of Medicine, vol. 340, No. 4:286-292, Jan. 28, 1999.

Hofer, et al., "The Unreliability of Individual Physician 'Report Cards' for Assessing the Costs and Quality of Care of a Chronic Disease", JAMA, Jun. 9, 1999, vol. 281, No. 22, pp. 2098-2105.

Ong et al, "The Colorectal Cancer Recurrence Support (CARES) System; Artificial Intelligence in Medicine", Nov. 1997, Elsevier, Netherlands, vol. 11, pp. 175-188.

Nahm, et al., "A Mutually Beneficial Integration of Data Mining and Information Extraction", In Proceedings of the Seventeenth National Conference on Artificial Intelligence (AAAI-2000), Jul. 30, 2000, pp. 627-632, Austin, TX, 20001.

Rao, et al., "Data mining for disease management: adding value to patient records", Electromedica, vol. 68, 2000, pp. 63-67.

Mills, "Computer Technology of the Not-Too-Distant Future" Sep. 1993, Medical Laboratory Observer, vol. 25, No. 9, p. 78.

Duda, et al., "Pattern Classification—Chapter 1" 2001, John Wiley & Sons, New York, US, XP002536377, pp. 14-17.

Hudson, et al., "The Feasibility of Using Automated Data to Assess Guideline-Concordant Care for Schizophrenia", Journal of Medical Systems, vol. 23 No. 4 1999, pp. 299-307.

PR Newswire, "Diabetes Health Management Award Honors Mayo Clinic's Zimmerman", Sep. 25, 2000, http://www.thefreelibrary.com/Diabetes Health Management Award Honors Mayo Clinic's Zimmerman.-a065465402.

Hudson, Mary E., "CAATS and compliance—computer-assisted audit techniques in health care", Internal Auditor, Apr. 1998, vol. 55, No. 2, p. 25, http://findarticles.com/p/articles/mi_m4153/is_n2_v55/ai_20860208/.

Grimes, Seth, "Structure, Models and Meaning, Is 'Unstructured' data merely unmodeled?", Intelligent Enterprise, Mar. 2005, http://intelligent-enterprise.informationweek.com/showArticle.jhtml?articleID=59301538.

Berkus, "Unstructured Data as an Oxymoron", ITtoolbox Blogs, Sep. 1, 2005, http://it.toolbox.com/blogs/database-soup/unstructured-data-as-an-oxymoron-5588.

Larsen, "Fast and Effective Test Mining Using Linear-time Document Clustering", In Knowledge Discovery and Data Mining (1999), pp. 16-22.

Rao, "From Unstructured Data to Actionable Intelligence", IT Pro, Nov./Dec. 2003, pp. 29-35.

Mitchell, "Machine Learning and Data Mining", Communications of the ACM, Nov. 1999, vol. 42, No. 11, pp. 31-36.

Kleissner, "Data Mining for the Enterprise", System Sciences, 1998, Proceedings of the Thirty-First Hawaii International Conference on Kohala Coast, HI, Jan. 6-9, 1998, IEEE Comput. Soc. US, pp. 295-304.

Evans, et al., "Using Data Mining to Characterize DNA Mutations by Patient Clinical Features", Proc AMIA Annu Fall Symp. 1997: 253-257.

Waltz, "Information Understanding Integrating Data Fusion and Data Mining Processes", Circuits and Systems, 1998, Proceedings of the 1998 IEEE International Symposium in Monterey, CA, USA, May 31-Jun. 3, 1998, NY, NY, May 31, 1998, pp. 553-556.

Roemer, et al., "Improved diagnostic and prognostic assessments using health management information fusion," AUTOTESTCON Proceedings, 2001. IEEE Systems Readiness Technology Conference , vol., no., pp. 365-377, 2001.

Chemical and Biological Arms Control Institute: "Bioterrorism in the United States:Threat, Preparedness and Response", Contract No. 200*1999*00132, Nov. 2000.

Hanson, et al.. "Probabilistic Heuristic Estimates", Annals of Mathematics and Artificial Intelligence, vol. 2, Nos. 1-4, pp. 209-220, 1990.

* cited by examiner

PATIENT DATA MINING FOR CARDIOLOGY SCREENING

CROSS REFERENCE TO RELATED APPLICATIONS

This application is a divisional of U.S. patent application Ser. No. 10/287,085, which claims the benefit of U.S. Provisional Application Ser. No. 60/335,542, filed on Nov. 2, 2001, which are incorporated by reference herein in their entirety.

FIELD OF THE INVENTION

The present invention relates to medical information processing systems, and, more particularly to a computerized system and method for screening patients for coronary heart disease (CHD), assessing a risk factor for a person to develop CHD and managing a person with CHD.

BACKGROUND OF THE INVENTION

Coronary heart disease is the number one killer in the western world. By detecting coronary heart disease as early as possible, appropriate, effective, and cost-effective treatment can be implemented.

However, cardiologists are faced with an ever-growing amount of data coming from a variety of different sources: imaging modalities, patient reports, ECG tracings, etc. As the number of information sources expand, extracting and assimilating all available data manually, and assessing various treatment options, becomes more and more difficult. Furthermore, with the push from managed care, cardiologists are expected to treat and manage more patients in the same amount of time.

Currently, there is considerable evidence that cardiovascular risk and disease is under-treated. Factors that account for this include gaps in knowledge, confusion over recommendations including target levels for lipids during treatment, poor doctor-patient communication, and variations in physician understanding and utilization of guidelines.

In view of the above, there exists a need for improved systems and methods for screening persons for coronary heart disease, assessing the risks of individuals patients in developing coronary heart disease, and managing patients with coronary heart disease.

SUMMARY OF THE INVENTION

A system and method for screening, detecting and managing patients with coronary heart disease (CHD) is provided.

According to one aspect of the present invention, a method for screening for coronary heart disease is provided including the steps of retrieving a test for assessing risk of coronary heart disease, the test including a plurality of data fields relating to coronary risk factors; accessing a database to populate the data fields of the test with patient information of an individual patient, the database including computerized patient records; and calculating a risk assessment of the individual patient developing coronary heart disease. The method further includes the steps of data mining information relating to the coronary risk factors from structured and unstructured data sources; and compiling the information as a structured computerized patient record in the database.

According to another aspect of the present invention, a coronary heart disease screening system includes a first database including a plurality of structured computerized patient records; a second database including a knowledge base relating to coronary heart disease, the second database including at least one test for determining coronary heart disease risk wherein the at least one test includes a plurality of data fields relating to coronary risk factors; and a processor for retrieving the at least one test from the second database, populating the data fields of the at least one test with patient information retrieved from the first database and calculating a risk assessment for at least one patient. The first database is compiled by data mining information relating to the coronary risk factors from structured and unstructured data sources.

According to a further aspect of the present invention, a program storage device readable by a machine, tangibly embodying a program of instructions executable by the machine to perform method steps for screening for coronary heart disease is provided. The method steps include retrieving a test for assessing risk of coronary heart disease, the test including a plurality of data fields relating to coronary risk factors; accessing a database to populate the data fields of the test with patient information of an individual patient, the database including computerized patient records; and calculating a risk assessment of the individual patient developing coronary heart disease.

BRIEF DESCRIPTION OF THE DRAWINGS

The above and other aspects, features and advantages of the present invention will become more apparent from the following detailed description when taken in conjunction with the accompanying drawings in which.

DESCRIPTION OF PREFERRED EMBODIMENTS

Figure 1:
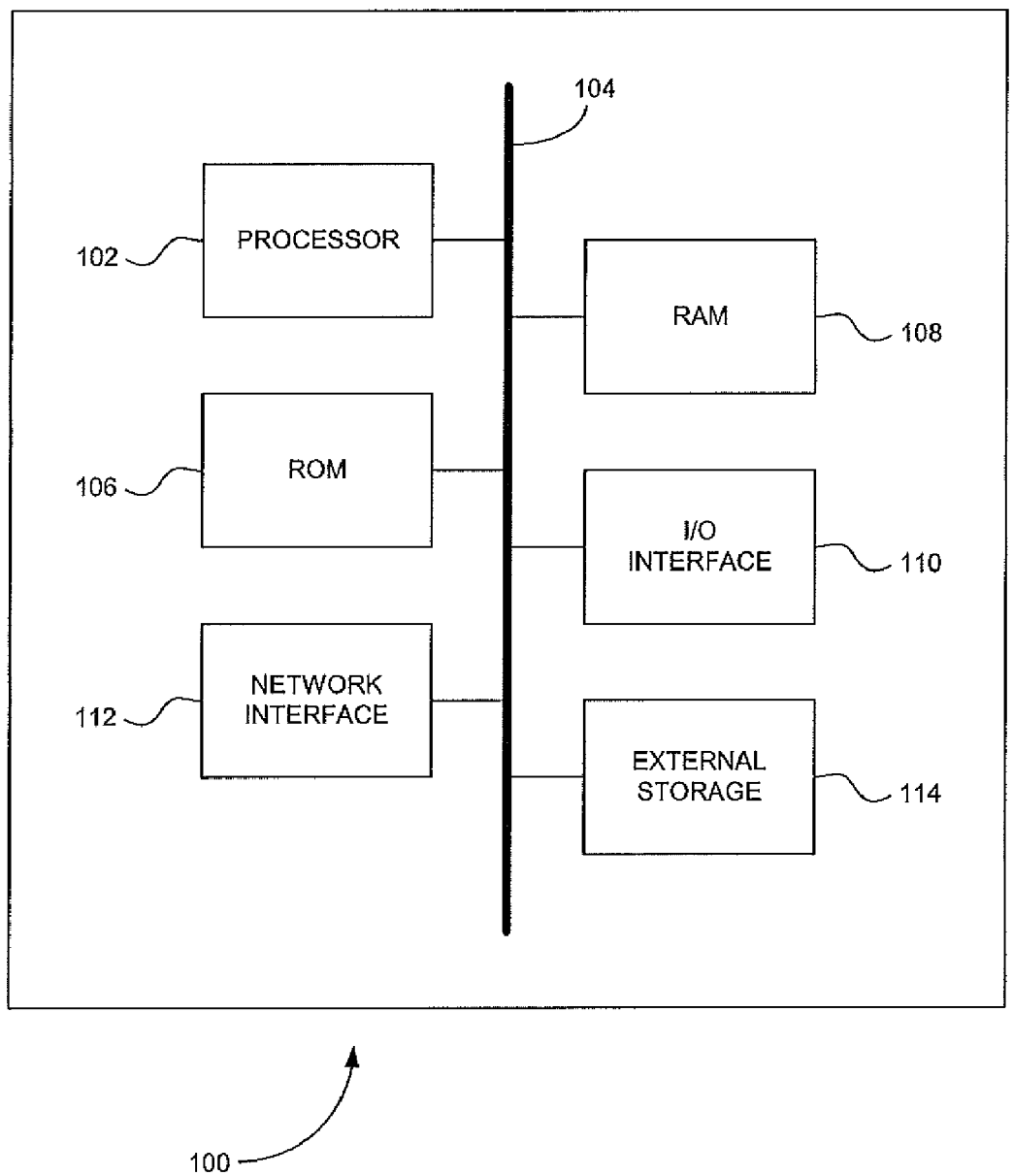
FIG. 1 is a block diagram of a computer processing system to which the present invention may be applied according to an embodiment of the present invention.

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

A system and method for screening, detecting and managing patients for coronary heart disease (CHD) is provided. According to an embodiment of the present invention, a computer-based coronary heart disease screening system will aid a physician in the assessment and management of coronary heart disease. First, the system will assimilate information from both imaging and non-imaging sources within a computerized patient record (CPR). These data can be automatically extracted, combined, an analyzed in a meaningful way, and the results presented to the physician. Such a system will also help avoid mistakes, as well as provide a novice with knowledge "captured" from expert users based on a domain knowledge base of a disease of interest and established clinical guidelines. Within each specific diagnostic test, the system will assist in automatically extracting information resulting in potential improvements to workflow as well as providing a powerful "second reader" in the evaluation of the results. Following evaluation, the system will also provide suggested therapies and follow-ups based on clinical guidelines. Finally, the system could track the patient over time, assessing the progress of the disease and the efficacy of therapy.

In the area of coronary artery disease, the world can be divided into two groups: those with known or suspected coronary artery disease, and those without. In the latter case, the key is to promote prevention and decrease the risk of coronary artery events. Here, the coronary heart disease screening system is targeted to the clinical cardiologist, and the general practitioner, to help assess, monitor, and reduce the risk of coronary heart disease.

In the case of people with known or suspected coronary heart disease, the role of a computer-aided coronary heart disease screening system is slightly different. First, such a system could aid in the assessment and diagnosis of the disease by the physician. Next, the system could help a cardiologist assess the severity of the disease, and help identify potential therapies. Finally, the system could assist with assessing the progression or regression of the disease either over time or in response to therapy.

It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
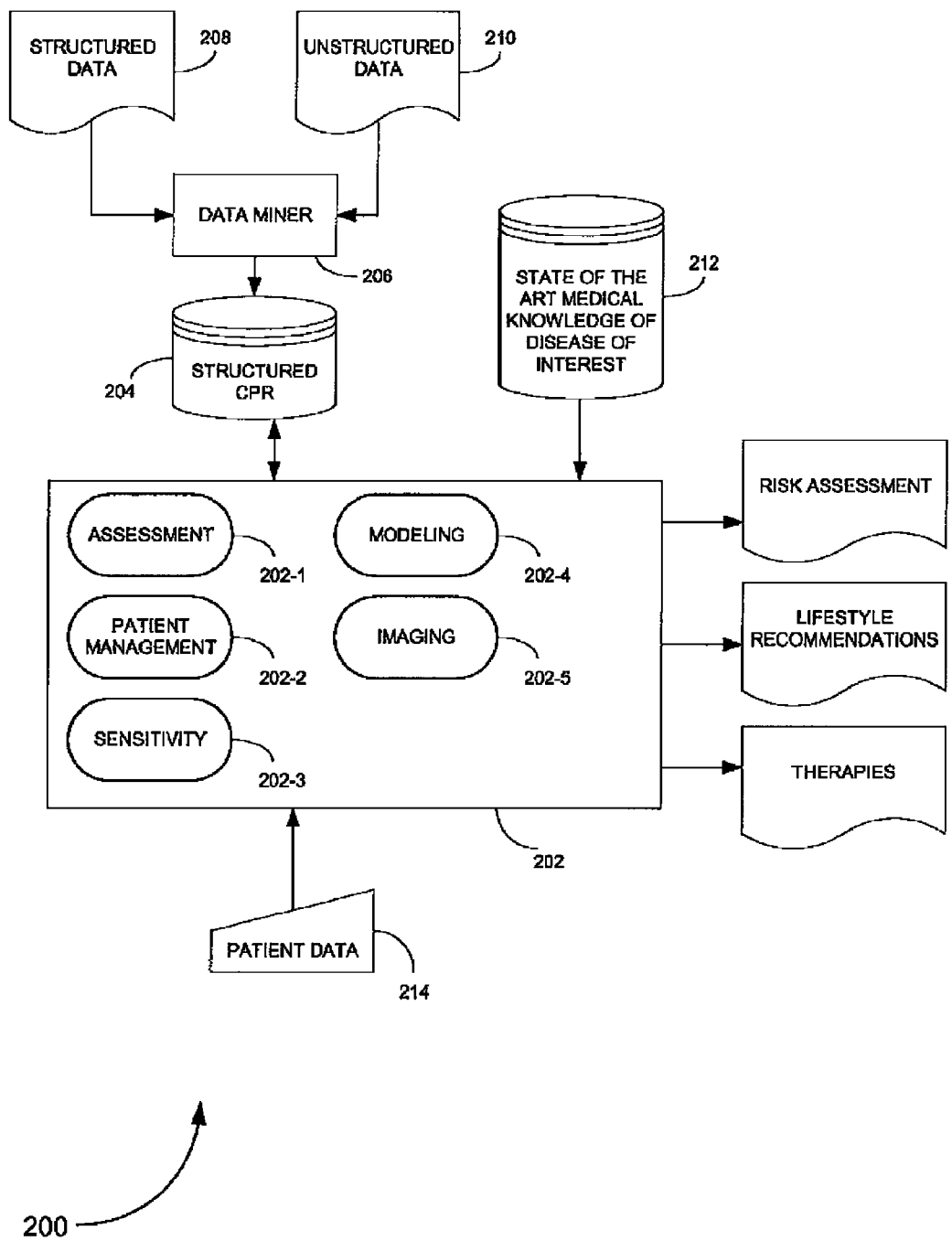
FIG. 2 illustrates an exemplary coronary heart disease screening system according to an embodiment of the present invention.

Referring to FIG. 2, an exemplary coronary heart disease (CHD) screening system 200 according to an embodiment of the present invention is illustrated. The CHD screening system 200 includes a processor 202 which processes a plurality of modules for performing different tasks. The processor is coupled to a first database 204 compiled to store a plurality of structured computerized patient records (CPR) relating to a disease of interest, here, coronary heart disease.

Preferably, the structured database 204 is populated with population-based patient information using data mining techniques described in "Patient Data Mining," by Rao et al., copending U.S. Published Patent Application No. 20030120458, filed Nov. 4, 2002, which is incorporated by reference herein in its entirety. That patent application teaches a data mining framework for mining high-quality structured clinical information. The data mining framework includes a data miner 206, having functions and capabilities as in the REMIND system, commercially available from Siemens Medical Solutions, that mines medical information from computerized patient records (CPRs) based on domain-specific knowledge contained in a knowledge base. The CPRs may be of structured 208 (e.g., chart, tables, billing information, etc.) and/or unstructured formats 210 (e.g., doctors' dictations, images such as MR (magnetic resonance) images and CT (computerized tomography) scans, ECG waveforms, etc.). The domain-specific knowledge may relate to a disease of interest, a hospital, etc. The data miner 206 includes components for extracting information from the CPRs, combining all available evidence in a principled fashion over time, and drawing inferences from this combination process. The mined medical information is stored in the structured CPR database, such as database 204.

The processor 202 is further coupled to a second database 212 including state of the art information relating to the disease of interest. This information may include standard procedures, established guidelines for treatment, standardized tests for assessment and diagnosis, etc.

Additionally, the processor 202 is adapted to receive manually inputted patient data 214 which it will process and store in the first structured database 204.

The CHD screening system 200 interacts with the first structured database 204 and the medical knowledge database 212 to assess the risk of a patient developing CHD, to recommend therapies and lifestyle changes to reduce the patient's assessed risk, and to perform sensitivity analysis to determine what factors are of the greatest risk to a patient. Each task performed by the CHD screening system 200 is performed by an executable module residing either in the processor of the system 202 and/or in a memory device (e.g., RAM, ROM, external storage, etc.) of the system.

Figure 3:
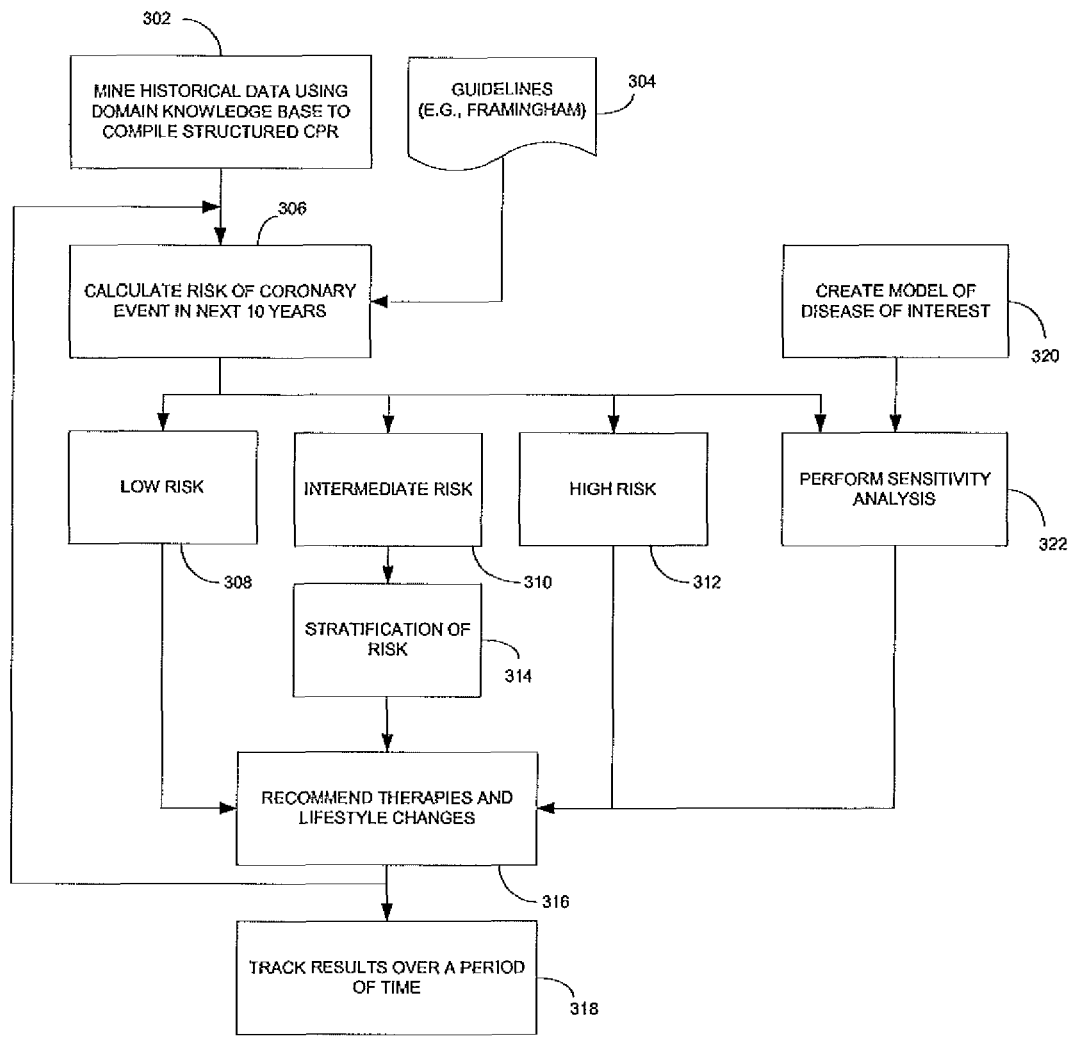
FIG. 3 illustrates a flow diagram for screening, monitoring and managing a patient according to an embodiment of the present invention.

Referring to FIGS. 2 and 3, the CHD screening system will be further described along with methods for assessing CHD risk, monitoring CHD patients and suggesting therapies and lifestyle changes.

The goal of both primary and secondary CHD prevention is to decrease the risk of subsequent acute coronary events, and thereby decrease mortality and prolong survival. In primary prevention, the idea is to identify healthy (asymptomatic) individuals at high risk of developing coronary artery disease, and initiate therapies and lifestyle changes to lower this risk. Secondary prevention does the same for people who have had an acute coronary event. The system and method of the present invention will assist physicians and play a significant role in assessment of risk, targeted suggestions for therapy and lifestyle changes based on established guidelines, and monitoring patient progress towards goals of risk reduction.

In primary prevention, asymptomatic individuals at high risk of developing coronary artery disease are identified, and therapies initiated and lifestyle changes recommended to lower this risk. First, asymptomatic patients are assessed for risk for coronary heart disease on the basis of risk factors. For example, the National Cholesterol Education Program (NCEP) has recently produced a set of Adult Treatment Panel (ATP III) guidelines for the treatment and management of lipid disorders. In these guidelines, the risk of an acute coronary event over a 10-year period for people with no history of coronary heart disease is calculated based on a modified version of the Framingham algorithm or test. The Framingham algorithm uses traditional risk factors, such as gender, obesity, smoking, total cholesterol, HDL-cholesterol, age, diabetes, and blood pressure, to determine overall risk. The ATP III guidelines also include other risk factors, such as family history and hypertension, in its risk model. In addition to these traditional risk factors, the guideline acknowledges emerging risk factors, such as hemocysteine, lipoprotein (a), and inflammatory markers such as high sensitivity C-reactive proteins which can indicate risk of acute coronary events. In addition, the NCEP ATP III has developed specific recommendations for therapy and lifestyle changes based on these risk factors for both primary and secondary prevention. Such tests, recommendations and guidelines will be stored in the medical knowledge database 212.

These guidelines serve to help the clinical cardiologist, as well as the patient's primary-care physician, assess the risk and help prevent the incidence of an acute coronary artery event. In this situation, the CHD screening system 200 could provide valuable assistance in a variety of different ways. First, the assessment of risk requires obtaining clinical information contained in a variety of different locations within a patient's record. Structured 208 and unstructured 210 data are mined via the data miner 206 and stored in structured CPR in database 204 (step 302). The system 200 then accessed the second database 212 to retrieve a test, such as the Framingham algorithm, to assess the risk of an individual patient (step 304). An assessment module 202-1 receives the test and populates a plurality of data fields within the test with information retrieved from the structured database 204 and calculates the risk for the patient (step 306). Depending on the risk assessment or score, the patient is categorized as being a low risk (step 308), intermediate risk (310) or high risk (step 312).

It is to be appreciated that all the information necessary to calculate the risk assessment may not be readily available from the patient record. If the information is missing, the system will mine available data to make a probabilistic assertion regarding the missing information. The system will then calculate the patient's risk assessment with the probabilistic information.

It is to be appreciated that the ability to automatically retrieve information and calculate these risks would save the physician time, and would enable automated screening of a very large population. Incomplete or conflicting information could be brought to the attention of the physician.

Once the risk is assessed for an individual patient, a specific set of recommended tests, therapies and/or lifestyle changes, targeted to the patient and based on specific adopted guidelines, will be automatically generated (step 316). Upon subsequent screening visits by the patient, the CHD system 200 will track recommendations against patient performance via a patient management module 202-2. For example, the patient's cholesterol levels and lifestyle changes in subsequent check-ups could be matched against guideline targets and previously recorded levels, and follow-up reports automatically generated for the physician. The patient management module may periodically reassess the risk of the patient and alert the appropriate personnel if a significant change is detected. Additionally, the patient management module may recommend a time for a reassessment due to the length of time between assessments and or tests.

In addition to assessing current risk, the CHD system 200 will perform sensitivity analysis on the various risk factors to assess the importance of each individual risk factor on that patient via a sensitivity module 202-3. That is, for each risk factor, the system will weigh its individual importance in assigning the overall risk of acute coronary events to the individual. First, a model is created to simulate a patient with similar characteristics of the patient being tested (step 320). A modeling module 202-4 generates the model either by simulating a similar patient based on the data stored in the medical knowledge database 212 or by mining data of similar patients from population-based data sources via the data miner 206 using a domain knowledge base of the disease of interest (i.e., coronary heart disease; alternatively, the model could be a combination of both. The sensitivity module 202-3 then interacts with the modeling module 202-4 by varying input data to simulate different scenarios to determine which factor most influences the risk assessment of the patient (step 322).

The sensitivity analysis is important for several reasons. First, for many patients, not all of the risk factors are usually tested. For example, one of the risk factors is the presence of diabetes. However, not all patients have had a blood-sugar test done. In this case, the risk of heart disease is first assessed without this information. Then, an analysis is done with different blood-sugar results to see whether the risk assessment outcome changes. If the change is significant, the system may recommend that a blood-sugar test be done to refine the cardiac risk for the patient. Secondly, the sensitivity analysis will assess when the patient needs to come back for another screening, and what exams should be performed (step 316). For example, it is known that blood pressure can change significantly from reading to reading, and it can also slowly go up or down over time. By knowing the typical variability of such a variable, the system can help decide when the patient needs to come back for another blood pressure reading by assessing what type of change would result in a significant change in risk assessment.

Additionally, the system 200 will recommend whether further risk stratification is needed. If the initial risk assessment shows that a person has a low risk of acute coronary events (step 308), then a physician may recommend a to healthy lifestyle with diet and exercise (step 316). Conversely, if the assessment shows a high risk of acute coronary event (step 312), then a physician may decide on some kind of therapy (316), such as aspirin or cholesterol-reducing drugs, based on clinical guidelines. However, some people will show an intermediate risk of heart disease (step 310). In these cases, there may be a need to further assess and refine the risk of coronary heart disease in a patient (step 314).

Where further risk stratification is needed, a number of different techniques can be used, and the choice of a technique may depend on the cardiologist's experience, comfort level, and access to equipment. Many of the techniques developed to further stratify risk do so by measuring artherosclerotic burden, for example, (1) measurement of ankle/brachial blood pressure index (ABI); (2) measurement of hemocysteine, lipoprotein (a), and inflammatory markers such as high sensitivity C-reactive proteins, as well as other emerging biochemical markers; (3) measurement of intima-media thickness (IMT) from the carotid arteries using high-frequency B-mode ultrasound; (4) assessment of plaques in coronary arteries using Electron-beam Computed Tomography (EBCT); (5) assessment of composition of artherosclerotic plaque with magnetic resonance imaging (MRI); (6) assessment of endothelial function to determine artheroscierotic risk; and (7) scoring coronary calcium, e.g., using the Agatston score.

To facilitate the risk stratification, the system 200 may further include an imaging module 202-5 to automatically extract information from the imaging sources mentioned above (e.g., by conventional image segmentation methods), and combine the extracted information with the previously assessed risk to reassess the overall risk of the patient. The results of any risk stratification could be used to generate patient-directed recommendations based on established clinical guidelines using this additional risk assessment (step 316).

Implementation of the CHD system for secondary prevention is a simpler than for primary prevention. The reason is that once a patient has had an acute coronary event, they will always be at high-risk for a subsequent event. Therefore, there is little need for risk assessment in these individuals. Rather, the main emphasis in secondary prevention is to create a specific set of recommended therapies and lifestyle changes, targeted to the patient and based on specific adopted guidelines.

Goals for lifestyle changes as well as lipid management and blood pressure have been established for primary and secondary prevention. By tracking a patient over time (step 318), the system could automatically assess whether the patient is achieving the desired goals for risk reduction, and whether changes need to be implemented either in the therapy or implementation. The effects of specific diet changes, exercise, or cholesterol-lowering drugs, for example, can be feedback into the system to redesign therapies and create new recommendations for individual patients. Conventionally, tracking patients require manual monitoring of patient information, and comparing against established standards. These manual monitoring techniques have resulted in inconsistent management of cardiovascular risk.

Furthermore, the CHD system can be used to assist in diagnosis of a patient with CHD. Often times, the first time a patient is referred to a cardiologist is after coronary artery disease has significantly progressed, and the patient exhibits some symptoms. For this group of people, it is important to be able to diagnose the disease, and then apply appropriate therapy and monitor their progress in a rapid manner. The diagnosis may be performed combining all available information about the patient and perform a probabilistic inference on patient-specific issues based on the domain knowledge base using techniques described in "Patient Data Mining for Diagnosis and Projections of Patient States," by Rao et al., copending U.S. Published Patent Application No. 20030126101, filed Nov. 4, 2002, which is incorporated by reference herein in its entirety.

For example, in an emergency room, patients may present with chest pain. The emergency room physician must be able to diagnose acute coronary events, and may need to initiate therapies to stabilize the patient. According to ACC/AHA guidelines, electrocardiography (ECG) is the procedure of first choice in patients presenting with chest pain, dizziness or syncope—symptoms that may be predictive of sudden death or myocardial infarction. In situations where the ECG is non-diagnostic, ultrasound can be used to assess regional systolic wall motion abnormalities. Since the emergency room physician may not be as experienced as a cardiologist to interpret these tests, the CHD system can provide a checklist of items to assist with diagnosis, and then automatically extract information from sources, such as the ECG or ultrasound exams, to assist in rapid determination of an acute coronary event. In addition, the system could provide suggested immediate therapies based on established clinical guidelines.

Furthermore, the CHD system could aid a clinical cardiologist in answering important clinical questions, including: diagnosis of obstructive coronary heart disease; assessment of severity of disease and complications; assessment of viability of diseased heart tissue; and recommendations for patient management based on established clinical guidelines.

A number of diagnostic tools are at the cardiologist's disposal to help answer these questions, e.g., electrocardiography, coronary angiography, radionuclide imaging, ultrasound, magnetic resonance imaging, electron-beam computed tomography, etc. Each of these modalities measures either direct or surrogate indicators of coronary artery disease. Individually, each can help provide evidence of coronary artery disease. The choice of diagnostic tool used by the cardiologist is often made based on availability, experience, and comfort level. Each modality measures something slightly different in assessing coronary artery disease. Potentially more powerful, therefore, is the registration of data from different sources to provide a more complete picture in assessing coronary artery disease. Currently, diagnosis of coronary artery disease is often done using a qualitative, or semi-quantitative, approach. As a result, the effectiveness of such diagnostic approaches depends to a great extent on the experience and knowledge of the doctor. For example, stress echocardiography for assessment for global function and regional abnormalities is done using a visual inspection followed by point scoring.

The CHD system will extract and combine information in a quantitative manner from a variety of different sources to help the clinical cardiologist address these clinical questions, augmenting the physician's own intuition and experience. In this manner, the system would assist the physician in their own decision-making process, following accepted guidelines and practices.

In addition to detecting coronary artery disease, a number of imaging modalities can be used to assess the progression or regression of the disease either over time or in response to therapy. Some of these include ultrasound, coronary angiography, radionuclide imaging, and intravascular ultrasound. Many times, these techniques are used to study the effects of specific therapy, such as revascularization. In another scenario, these techniques could be used to monitor the progression or regression of a patient over time to assess when and if intervention is necessary.

The CHD system will extract information from the images produced, e.g., by segmentation, volume rendering, etc., and register the information on a patient from different points of time and from different sources, to assess the progression or regression of disease. By creating such an automatic system, physicians can more easily monitor the progression or regression of coronary artery disease, which can assist in deciding the efficacy of a particular plan of treatment.

In the area of coronary artery disease, the systems and methods of the present invention can potentially play a large role in the total management of a patient, including prevention, detection, therapy, and monitoring. Today, information about the patient comes a wide variety of different sources, including patient clinical history, waveform data such as ECG, imaging data, blood tests, etc. Furthermore, numerous clinical guidelines are established by bodies such as the ACC, AHA, and ESC to discuss issues such as prevention, detection, and therapy. The system and method of the present invention can assist physicians by automatically collecting information from a wide variety of different sources and analyzing them. Information can be presented to the physician along with suggestions based on established clinical guidelines.

It is to be appreciated that various embodiments of the present invention are to be defined in the context of the physician's workflow. Such embodiments could exist as a distributed system within different sub-systems as defined by clinical workflow and usefulness. For example, some components may fit within the imaging modality, such as on the ultrasound system or on an MRI console system. Other pieces or components may reside on a review workstation, like a KinetDx® or Leonardo™ workstation. A comprehensive system may belong on a Sorian™ cardiology system. Together, they will form a united clinical solution. Alternatively, such a system could exist as a remote server resulting in an ASP (Application Service Provider)-model solution. This could allow small systems, such as hand-held ultrasound systems and other hand-held devices (e.g., personal digital assistants, handheld computers, laptop computers, etc.) to leverage the CHD system at a remote site, in an emergency room or at the scene of an incident outside the hospital.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A coronary heart disease screening system comprising:
a first database including a plurality of structured computerized patient records mined, at least in part, form an unstructured data source using probabilistic inference, a first of the structured computerized patient records having patient information for a plurality of coronary risk factors for a patient;
a second database including a knowledge base relating to coronary heart disease, the second database including at least one test for determining coronary heart disease risk wherein the at least one test includes a plurality of data fields relating to the coronary risk factors; and
a processor for retrieving the at least one test from the second database, populating the data fields of the at least one test with patient information retrieved from the first database and calculating a risk assessment for the patient.

2. The system as in claim 1, wherein the first database is compiled by data mining information relating to the coronary risk factors from structured and unstructured data sources.

3. The system as in claim 1, further comprising an assessment module for determining whether the patient has a low risk, intermediate risk or high risk of developing coronary heart disease based on the calculated risk assessment.

4. The system as in claim 3, wherein if the individual patient is determined to be an intermediate risk, the processor is adapted to stratify the risk assessment by data mining information measuring atherosclerotic burden from the structured computerized patient record of the patient.

5. The system as in claim 1, further comprising a patient management module for recommending lifestyle changes to the patient based on the calculated risk assessment.

6. The system as in claim 5, wherein the patient management module tracks the patient over a period of time and recalculates the risk assessment of the patient.

7. The system as in claim 1, further comprising a patient management module for recommending therapies to the patient based on the calculated risk assessment.

8. The system as in claim 7, wherein the patient management module tracks the patient over a period of time and recalculating the risk assessment of the patient.

9. The system as in claim 1, further comprising a sensitivity module for analyzing the coronary risks factors of the patient to determine which factor will have the greatest effect in influencing the risk assessment.

10. The system as in claim 9, further comprising a modeling module for generating a model of a coronary heart disease patient to simulate effects of different variables, the model being employed by the sensitivity module.

11. The system as in claim 1, further comprising an imaging module for extracting patient information from images and storing the patient information in the structured computerized patient record.

12. The system as in claim 1, wherein the processor determines a time for a follow-up assessment based on the calculated assessment.

13. The system as in claim 1, wherein the processor determines if at least one of the plurality of data fields is not populated and recommends a test to be conducted to populate the at least one data field.

14. The system as in claim 9, wherein the processor determines a time for a follow-up assessment based on the determined risk factor.

15. The system as in claim 9, wherein the processor determines if at least one of the plurality of data fields is not populated and recommends a test to be conducted if the at least one data field is the determined risk factor.

16. The system as in claim 1, wherein at least one of the plurality of structured patient records include information obtained from mining unstructured data.

17. The system of claim 1, wherein the plurality of structured patient records include probabilistic information for the patient information of the coronary risk factors.

18. The systems of claim 1, wherein all the patient information needed to calculate the risk assessment is not included in the plurality of structured patient records.

19. The system of claim 8, wherein missing information is mined probabilistically and the risk assessment is adjusted to include the probabilistic patient information in the risk assessment.

20. The system of claim 19, wherein the risk assessment is computed automatically at periodic intervals from the patient record.

21. The system of claim 20, wherein the processor notifies if there is a significant change in the patient's risk assessment.

22. The system of claim 21, wherein the processor notifies if sufficient time has lapsed such that it is possible the patient's risk assessment has significantly changed.

23. The system of claim 1 wherein the processor is configured to recommend tests, therapies, lifestyle changes, or combinations thereof as a function of analysis of the populated data field and a medical guideline.

24. The system of claim 1 wherein the processor is configured to assist in following a guideline.

* * * * *